United States Patent [19]

Commeyras et al.

[11] 4,387,254

[45] Jun. 7, 1983

[54] PROCESS FOR THE PREPARATION OF IODOALCOHOLS HAVING A PERFLUOROALKYL CHAIN

[75] Inventors: Auguste Commeyras, Clapiers; René Sagnes; Claudine Guery, both of Montpellier, all of France

[73] Assignee: Produits Chimiques Ugine Kuhlmann, Courbevoie, France

[21] Appl. No.: 278,703

[22] Filed: Jun. 29, 1981

[30] Foreign Application Priority Data

Jul. 8, 1981 [FR] France ................................ 80 15122

[51] Int. Cl.$^3$ .............................................. C07C 31/34
[52] U.S. Cl. ................................ 568/842; 252/431 C; 252/441
[58] Field of Search ........................................ 568/842

[56] References Cited

U.S. PATENT DOCUMENTS 3,145,222  8/1964  Brace ............................... 568/842 X
3,257,407  6/1966  Brace ............................... 568/842 X

FOREIGN PATENT DOCUMENTS 2103459  4/1972  France .
1017978  1/1966  United Kingdom .

Primary Examiner—Howard T. Mars
Attorney, Agent, or Firm—Sigalos & Levine

[57] ABSTRACT

The process for the preparation of iodoalcohols having a perfluoroalkyl chain by the reaction of iodoperfluoroalkanes with unsaturated alcohols, in which the reaction is carried out in the presence of a catalyst pair selected from mercurous iodide/mercuric iodide, mercurous acetate/mercuric iodide, or manganous acetylacetonate/manganic acetylacetonate.

4 Claims, No Drawings

PROCESS FOR THE PREPARATION OF IODOALCOHOLS HAVING A PERFLUOROALKYL CHAIN

BACKGROUND OF THE INVENTION

The process of the invention concerns the preparation of iodoalcohols having a perfluoroalkyl chain.

This process consists of adding a perfluoroalkane iodide $CF_3(CF_2)_nI$, which is designated herein by the generic term "$R_FI$", onto an ethylenic alcohol.

Various processes are known which permit the reaction of $R_FI$ iodides with ethylenic compounds. However, these processes give only mediocre yields in the case of ethylenic alcohols and especially in the case of allyl alcohol.

This reaction can, for instance, be carried out by the use of radicals initiating the reaction by an elevation of temperature (R. N. Haszeldine, J. Chem. Soc. 1953, p. 1199; U.S. Pat. Nos. 3,016,406 and 3,016,407), by irradiation with ultraviolet rays (R. N. Haszeldine's article cited above; J. D. Park, J. Org. Chem. 26, 1961, p. 2086, and C. Cantacuzene, J. Chem. Soc. Perkin I, 1977, p. 1365), or by the use of azoic derivatives (N. O. Brace, J. Org. Chem. 27, 1962, p. 3027 and U.S. Pats. Nos. 3,083,224, 3,145, 222, and 3,257,407).

It is likewise possible to catalyze the addition by Assher's system (J. Chem. Soc. 1961, p. 2261), with the catalyst being a mixture of cuprous and cupric salts and of amines. This process was extended to fluorinated molecules by D. J. Burton (Tetrahedron Letters 1966, p. 5163), N. O. Brace (J. Org. Chem. 44, 1979, p. 212) and described in French Pat. No. 2,103,459.

Although all of these systems make it possible to reach $R_FI$ with an ethylenic compound, they present the drawback of resulting only in mediocre (low) and very variable yields, depending on the nature of the initiator and the nature of the olefin used. A universal catalyst does not exist and, in particular, there is no system capable of causing the quantitative addition of $R_FI$ onto ethylenic alcohols. Thus, the photochemical addition according to J. D. Park, or the process described in French Pat. No. 2,103,459, yield a degree of conversion of only 50–55% with allyl alcohol.

SUMMARY OF THE INVENTION

A process has now been found which overcomes the problems of the prior art and gives consistent high yields.

Briefly, the present invention comprises the process for the preparation of an iodoalcohol having a perfluoroalkyl chain comprising reacing an iodoperfluoroalkane with an unsaturated alcohol in the presence of a catalyst pair selected from mercurous iodide/mercuric iodide, mercurous acetate/mercuric iodide, or manganous acetylacetonate/manganic acetylacetonate.

DETAILED DESCRIPTION

The catalyst pairs of the present invention make it possible to operate at a temperature close to the ambient temperature and the practically quantitative addition of $R_FI$ onto ethylenic alcohols and, in particular, onto allyl alcohol.

The reaction is preferably carried out in the presence of an excess of alcohol which can play the role of solvent, dimethylformamide (DMF), for instance, resulting in an increased rate of reaction. The latter generally is very rapid and it is possible, in particular, to obtain quantitative transformations in the case of allyl alcohol with reaction times of the order of 2 hours.

The various parameters, namely the alcohol excess, $Hg^{++}/Hg^+$ ratio, $Hg/R_FI$ ratio and the temperature, are not critical. Nevertheless, in order to obtain quantitative yields with the shortest possible reaction durations, it is preferable to use an excess of alcohol and a $Hg^+/Hg^{++}$ ratio below 1. Also, the reaction rate increases with the temperature, but in practice it is unnecessary to exceed temperatures of the order of 35° to 40° C.

The length of the perfluoroalkyl chain has only little effect on the yield and on the reaction rate. The reaction must be stopped as soon as the $R_FI$ has been consumed entirely, otherwise the iodohydrin having been formed risks being degraded.

The most efficacious pairs are mercurous/mercuric iodides, mercurous acetate/mercuric iodide, and the pair of acetylacetonates of $Mn^{++}/Mn^{3+}$.

With allyl alcohol and the α,ω-unsaturated alcohols, a single isomer is obtained according to the reaction:

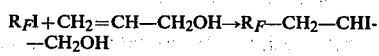

$$R_FI + CH_2=CH-CH_2OH \rightarrow R_F-CH_2-CHI-CH_2OH$$

On the other hand, with the alcohols having an internal double bond or a substitution on the adjacent carbon atom, whether they be primary alcohols or secondary alcohols, a mixture of isomers is obtained.

All of these polyfluorinated halohydrin products are intermediates and can be used for the manufacture of fluorinated surfactants and for obtaining hydropholic and oleopholic derivatives which are useful, in particular, for the treatment of textiles, leather, paper, and the like.

The invention will be further described in connection with the following examples, which are set forth for purposes of illustration only.

EXAMPLE 1

0.1 mole (5.8 g) of allyl alcohol, 5 ml of DMF, $1.5 \times 10^{-3}$ moles (0.98 g) of $Hg_2I_2$, $3 \times 10^{-3}$ moles (1.36 g) of $HgI_2$ and $20 \times 10^{-3}$ moles (8.92 g) of $C_6F_{13}I$ are placed into a reactor of 250-ml capacity having a magnetic agitator.

The temperature is raised to 35° C. At the end of 1 hour and 30 minutes, all of the $R_FI$ has been consumed and converted into the addition product $C_6F_{13}-CH_2-CHI-CH_2OH$. The yield, as verified by vapor-phase chromatography and NMR ($H'$ and $F^{19}$) is quantitative.

It is possible to separate the reaction product by pouring the reaction mixture into 250 ml of water. The dense, heavy layer is decanted and extracted with $CCl_4$, $17 \times 10^{-3}$ moles (8.57 g) of iodohydrin are obtained (85% yield), which is in the form of a white sublimable solid having a melting point of 49° C.

EXAMPLES 2 TO 5

Various operations are carried out by changing the parameters of the reaction and the length of the perfluorinated chain.

The results are recapitulated in Table I. The iodohydrin based on $C_4F_9$ is in the form of a liquid having a boiling point of 70°–75° C. under a pressure of 2 Torr, while the iodohydrin based on $C_8F_{17}$ is in the form of a white sublimable solid having a melting point of 82° C.

TABLE I

| Examples | 2 | 3 | 4 | 5 |
|---|---|---|---|---|
| Allyl alcohol/$R_FI$ (mole/mole) | 5 | 5 | 5 | 5 |
| $R_FI/Hg_2I_2$ (mole/mole) | 13.3 | 26.6 | 9 | 13.3 |
| $Hg_2I_2/HgI_2$ (mole/mole) | 0.25 | 0.125 | 0.5 | 0.25 |
| DMF cc/mole $R_FI$ | 250 | 250 | 250 | 250 |
| $R_F$ | $C_4F_9$ | $C_4F_9$ | $C_4F_9$ | $C_8F_{17}$ |
| T° C. | 35 | 35 | 35 | 35 |
| Conversion of the $R_FI$ into addition products | 100% | 100% | 100% | 100% |
| Total reaction time in hours | 1.4 | 1.5 | 2 | 1.5 |

EXAMPLES 6 TO 11

Example 2 is repeated, but by operating with various alcohols. The results are shown in Table II below.

TABLE II

| Example | Alcohol | Duration | Number of Alcohols being Geometrical Isomers | Degree of Conversion of the $R_FI$ into Addition Product |
|---|---|---|---|---|
| 6 | 1-butene-4-ol | 4 hours | 1 | 100% |
| 7 | 4-pentene-1-ol | ~4 days | 2 | 100% |
| 8 | 2-butene-1-ol | 4 hours 30 min. | 3 | 100% |
| 9 | 3-hexene-1-ol | 7 days | 4 | 95% |
| 10 | 3-butene-2-ol | 2 hours | 2 | 99% |
| 11 | methylallyl alcohol | 4 days | 2 | 95% |

EXAMPLE 12

Under the experimental conditions of Example 2, but by operating at 50° C. and by replacing the mercury salts with equivalent quantities of the acetylacetonates of $Mn^{3+}$ and $Mn^{2+}$, after a reaction duration of 96 hours, the conversion of $C_4F_9I$ into 3-(perfluorobutyl)-2-iodopropanol, i.e., $R_F$—$CH_2$—$CHI$—$CH_2OH$, is a total conversion.

While the invention has been described in connection with preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A process for the preparation of an iodoalcohol having a perfluoroalkyl chain comprising reacting an iodoperfluoroalkane with an ethylenic alcohol in the presence of a catalyst pair selected from mercurous iodide/mercuric iodide, mercurous acetate/mercuric iodide, or manganous acetylacetonate/manganic acetylacetonate.

2. The process of claim 1, in which the reaction temperature is between 35° and 40° C.

3. The process of claim 1 or 2, in which the ethylenic alcohol is allyl alcohol.

4. The process of claim 1 or 2, in which the ethylenic alcohol is allyl alcohol and the catalyst pair is mercurous iodide/mercuric iodide.

* * * * *